(12) United States Patent
Angel et al.

(10) Patent No.: US 9,040,065 B2
(45) Date of Patent: May 26, 2015

(54) PREPARATION OF POLYACRYLATES BY EMULSION POLYMERIZATION

(75) Inventors: Maximilian Angel, Schifferstadt (DE); Peter Hossel, Schifferstadt (DE)

(73) Assignee: BASF SE, Ludwigshafen (DE)

( * ) Notice: Subject to any disclaimer, the term of this patent is extended or adjusted under 35 U.S.C. 154(b) by 236 days.

(21) Appl. No.: 13/489,932

(22) Filed: Jun. 6, 2012

(65) Prior Publication Data

US 2012/0315238 A1 Dec. 13, 2012

Related U.S. Application Data

(60) Provisional application No. 61/493,983, filed on Jun. 7, 2011.

(51) Int. Cl.

| | |
|---|---|
| *C08F 2/22* | (2006.01) |
| *C08F 220/18* | (2006.01) |
| *A61Q 5/06* | (2006.01) |
| *A61K 8/81* | (2006.01) |
| *C08F 220/28* | (2006.01) |
| *A61Q 5/00* | (2006.01) |
| *A61Q 5/02* | (2006.01) |
| *A61Q 5/10* | (2006.01) |
| *A61Q 5/12* | (2006.01) |

(52) U.S. Cl.
CPC ............ *C08F 2/22* (2013.01); *C08F 220/18* (2013.01); *C08F 2220/286* (2013.01); *A61Q 5/006* (2013.01); *A61Q 5/02* (2013.01); *A61Q 5/06* (2013.01); *A61Q 5/10* (2013.01); *A61Q 5/12* (2013.01); *A61K 8/8152* (2013.01); *A61K 8/8158* (2013.01); *A61K 2800/48* (2013.01)

(58) Field of Classification Search
None
See application file for complete search history.

(56) References Cited

U.S. PATENT DOCUMENTS

| | | | |
|---|---|---|---|
| 5,436,292 | A | 7/1995 | Jenkins et al. |
| 7,790,800 | B2 | 9/2010 | Suau et al. |
| 2008/0103248 | A1* | 5/2008 | Suau et al. ............... 524/548 |
| 2008/0194715 | A1 | 8/2008 | Wendel et al. |
| 2008/0199416 | A1 | 8/2008 | Nguyen-Kim et al. |
| 2010/0210771 | A1 | 8/2010 | Leyrer et al. |

FOREIGN PATENT DOCUMENTS

| | | |
|---|---|---|
| EP | 13836 | 8/1980 |
| EP | 0761780 | 3/1997 |
| WO | WO-99/65958 | 12/1999 |
| WO | WO-2006/016035 | 2/2006 |
| WO | WO-2006/106114 | 10/2006 |
| WO | WO-2006/106140 | 10/2006 |
| WO | WO-2007/010035 | 1/2007 |
| WO | WO-2009/062994 | 5/2009 |

OTHER PUBLICATIONS

PCT International Preliminary Report on Patentability and Written Opinion in PCT/EP2012/058416, dated Dec. 10, 2013, 6 pages.
PCT International Search Report in PCT/EP2012/058416, dated Jun. 12, 2012, 2 pages.
Kosmetik und Hygiene von Kopf bis Fuss (Cosmetics and Hygiene from Head to Toe), Umbach, Wilfried (ed.), 3$^{rd}$ Edition, Viley-VCH, 2004, 123-128.
Kosmetik und Hygiene von Kopf bis Fuss (Cosmetics and Hygiene from Head to Toe), Umbach, Wilfried (ed.), 3$^{rd}$ Edition, Viley-VCH, 2004, 235-236.

* cited by examiner

*Primary Examiner* — Brian Gulledge
(74) *Attorney, Agent, or Firm* — Servilla Whitney LLC

(57) ABSTRACT

The present invention relates to a process for the preparation of polymers comprising carboxyl groups by emulsion polymerization and the use of the polymers obtainable by this process, for example as thickeners. Moreover, the invention relates to thickener dispersions obtainable by the process and to the use thereof for modifying the rheology of paper coating slips, textile printing pastes, drugs, cosmetic preparations, detergents, cleansing compositions, or foods.

19 Claims, 1 Drawing Sheet

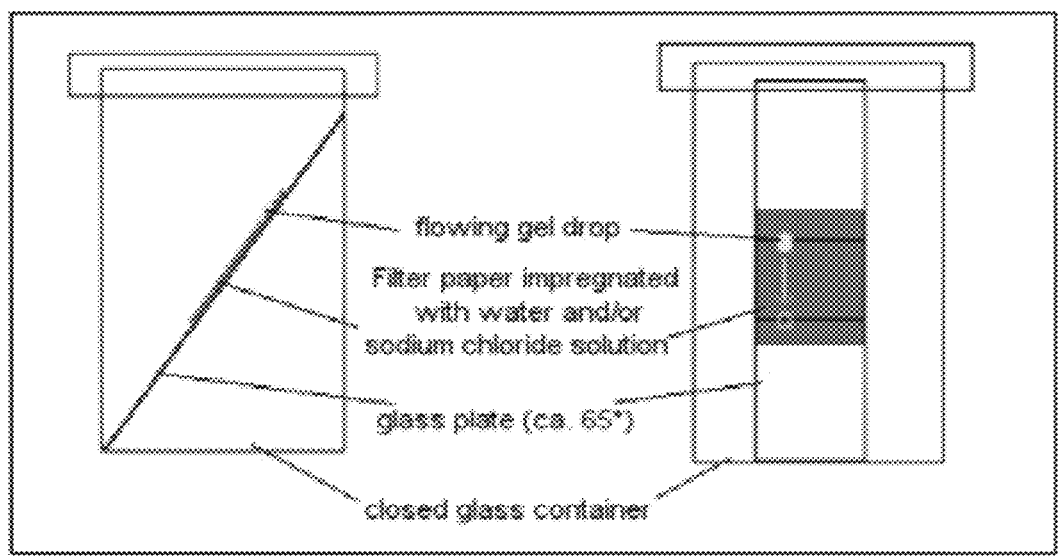
Experimental set-up salt stability/inclined plane

PREPARATION OF POLYACRYLATES BY EMULSION POLYMERIZATION

CROSS-REFERENCE TO RELATED APPLICATIONS

This application claims the benefit of priority of U.S. Provisional Application No. 61/493,983 filed on Jun. 7, 2011, the entire content of which is hereby incorporated by reference in its entirety.

TECHNICAL FIELD

The present invention relates to a process for the preparation of polymers comprising carboxyl groups by emulsion polymerization and the use of the polymers obtainable by this process, for example as thickeners. Moreover, the invention relates to thickener dispersions obtainable by the process and to the use thereof for modifying the rheology of paper coating slips, textile printing pastes, drugs, cosmetic preparations, detergents, cleansing compositions or foods.

BACKGROUND

EP 13836 discloses emulsion copolymers, which comprise (i) 20 to 69.5% by weight of (meth)acrylic acid, (ii) 0.5 to 25% by weight of a monomer of the formula $CH_2=C(R)-C(O)-(CH_2CH_2O)_n-R^0$, in which R is H or $CH_3$, n is at least 2 and $R^0$ is $C_8-C_{30}$-alkyl, and (iii) at least 30% by weight of a $C_1-C_4$-alkyl(meth)acrylate. Following neutralization with alkali, these copolymers serve as thickeners for coating compositions, detergents and the like.

WO 99/65958 describes alkali-soluble thickeners, which comprise the reaction product of an unsaturated carboxylic acid, of a monoethylenically unsaturated monomer and of a hydrophobic, alkoxylated macromonomer. The monoethylenically unsaturated monomer comprises a methyl group; preferably, this is methyl acrylate. These polymers are said to become soluble at pHs of just 4.5 to 6.0 and are therefore suitable for cosmetic products.

WO 2006/016035 relates to the use of a water-soluble acrylic polymer as thickener in pigmented aqueous preparations. The acrylic polymer consists of an ethylenically unsaturated monomer with carboxyl function, an ethylenically unsaturated nonionic monomer and an ethylenically unsaturated oxyalkylated monomer, which is terminated with a hydrophobic non-aromatic branched chain having 10 to 24 carbon atoms.

WO 2009/062994 relates to a process for the preparation of an aqueous thickener dispersion from a monomer composition which comprises:
a) at least one ethylenically unsaturated carboxylic acid, and
b) at least one ethylenically unsaturated hydrophobic monomer, where
  (i) an at least partially polymerized pre-emulsion is prepared from 10 to 80% by weight, preferably 40 to 70% by weight, of the monomer composition and
  (ii) the remainder of the monomer composition is added in its entirety to the at least partially polymerized pre-emulsion and a free-radical polymerization is initiated.

The preparation of polymers with comparatively large amounts of carboxyl groups by the route of conventional emulsion polymerization often leads to the formation of coagulate or wall deposit within the reaction space, as a result of which the preparation process is generally hindered considerably.

The formation of finely divided coagulate, also referred to as microcoagulate or specks leads, inter alia, to the blockage of the filters used in the work-up of the dispersions. Specks cannot be seen in the liquid dispersion with the naked eye, but can generally not be separated off by conventional filtration. They adversely affect the further processing of the dispersions such as, for example, the manufacture of cosmetic preparations.

SUMMARY

Embodiments of the present invention are directed to a process for the preparation of polymers comprising, in polymerized-in form (a) M1a+M2a=30 to 70% by weight of an ester of (meth)acrylic acid with a $C_1-C_4$-alcohol; (b) M1b+M2b=30 to 70% by weight of (meth)acrylic acid; (c) M1c+M2c=0.1 to 20% by weight of monomer substituted with at least one $C_8-C_{30}$-radical; (d) M1d+M2d=0 to 20% by weight of monomers different from (a) to (c), by emulsion polymerization with a first polymerization stage and a second polymerization stage, wherein M1b/M1a≥0.4 and M1b/M1a<M2b/M2a and $$\sum_{i=a}^{d} M1i \leq 40\% \text{ by weight,}$$

where M1i are the respective weight fractions of the monomers (a) to (d), which are present in the reaction space during the first polymerization stage and M2i are the respective weight fractions of the monomers (a) to (d), which are added during the second polymerization stage and the sum of all weight fractions $$\sum_{i=a}^{d} M1i + \sum_{i=a}^{d} M2i = 100\% \text{ by weight.}$$

In one or more embodiments, (a) comprises ethyl acrylate. Component (b) can comprise methacrylic acid.

In one or more embodiments, (c) is 0.1 to 20% by weight of an ester of (meth)acrylic acid with at least one alcohol of general formula (I)

$$H-(O-CHR-CH_2)_x-O-C_yH_{2y+1} \quad (I)$$ 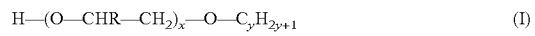

where x is an integer from 10 to 50, y is an integer from 12 to 30 and R is selected from H and $CH_3$, are present in polymerized-in form.

In a specific embodiment, (c) comprises at least two different monomers of the formula (I). y can be an interger from 16 to 22.

In one or more embodiments, the emulsion polymerization is carried out at a pH<7.

In one or more embodiments, the emulsion polymerization is carried out at a pH<5.

In one or more embodiments, $$\sum_{i=a}^{d} M1i \le 25\% \text{ by weight.}$$

A second aspect of the present invention is directed to a method of preparing an aqueous preparation, the method comprising using the polymer obtained by the process of the invention as a thickener.

A further aspect of the present invention is directed to a cosmetic composition comprising at least one polymer obtainable by the process of the present invention.

BRIEF DESCRIPTION OF THE DRAWINGS

The FIGURE is a depiction of the experimental set-up according to one or more embodiments of the present invention.

DETAILED DESCRIPTION

In one or more embodiments, the present invention provides a process which does not have the aforementioned disadvantages.

In one or more embodiments, the present invention provides polymers with rheology-modifying properties which are soluble in an aqueous medium at pH>7, preferably pH>8 with a concentration of at least 1 g per liter, preferably at least 10 g per liter, clear to the human eye and without visible clouding.

In one or more embodiments, the present invention provides polymers with rheology-modifying properties which permit the preparation of clear gels.

These objects are achieved by a process for the preparation of polymers comprising, in polymerized-in form
a) M1a+M2a=30 to 70% by weight of an ester of (meth) acrylic acid with a $C_1$-$C_4$-alcohol,
b) M1b+M2b=30 to 70% by weight of (meth)acrylic acid,
c) M1c+M2c=0.1 to 20% by weight of monomer substituted with at least one $C_8$-$C_{30}$-radical,
d) M1d+M2d=0 to 20% by weight of monomers different from a) to c), by emulsion polymerization with a first polymerization stage and a second polymerization stage, wherein
M1b/M1a≥0.4 and
M1b/M1a<M2b/M2a and $$\sum_{i=a}^{d} M1i \le 40\% \text{ by weight,}$$

where
M1i are the respective weight fractions of the monomers a) to d), which are present in the reaction space during the first polymerization stage and M2i are the respective weight fractions of the monomers a) to d), which are added during the second polymerization stage and the sum of all weight fractions $$\sum_{i=a}^{d} M1i + \sum_{i=a}^{d} M2i = 100\% \text{ by weight.}$$

Monomers a)

The monomers a) used are esters of (meth)acrylic acid with a $C_1$-$C_4$-alcohol. The $C_1$-$C_4$-alkyl (meth)acrylate is preferably selected from methyl (meth)acrylate, ethyl(meth)acrylate, n-propyl (meth)acrylate, isopropyl (meth)acrylate, n-butyl (meth)acrylate, isobutyl (meth)acrylate, sec-butyl (meth) acrylate, tert-butyl (meth)acrylate and any desired mixtures thereof.

In one or more embodiments, monomer a) is selected from methyl (meth)acrylate and ethyl (meth)acrylate. In a specific embodiment, monomer a) is ethyl acrylate.

Preferably, a) consists of at least 50% by weight, particularly preferably of at least 80% by weight and in particular of at least 90% by weight, of ethyl acrylate. In one embodiment of the invention, a) is or comprises ethyl acrylate.

The weight fraction of the monomers a), which is used in the first polymerization stage, based on the total amount of all monomers to be polymerized during the process according to the invention, is given by M1a.

The weight fraction of the monomers a), which is used in the second polymerization stage, based on the total amount of all monomers to be polymerized during the process according to the invention, is given by M2a.

The total weight fraction of the monomers a), based on the total amount of all monomers to be polymerized during the process according to the invention, is accordingly given by M1a+M2a and is in the range M1a+M2a=30-70% by weight, preferably 30-60% by weight, further preferably 40-50% by weight.

Monomers b)

(Meth)acrylic acid is used as monomer b). The term "(meth)acrylic acid" in the present case refers to acrylic acid, methacrylic acid, and mixtures thereof. The term (meth) acrylic acid here comprises in each case both the neutral and also the neutralized, anionic form of (meth)acrylic acid.

Preferably, b) consists of at least 50% by weight, particularly preferably of at least 80% by weight and in particular of at least 90% by weight, of methacrylic acid. In one embodiment of the invention, b) is or comprises methacrylic acid.

The weight fraction of the monomers b), which is used in the first polymerization stage, based on the total amount of all monomers to be polymerized during the process according to the invention, is given by M1b.

The weight fraction of the monomers b), which is used in the second polymerization stage, based on the total amount of all monomers to be polymerized during the process according to the invention, is given by M2b.

The total weight fraction of the monomers b), based on the total amount of all monomers to be polymerized during the process according to the invention, is accordingly given by M1b+M2b and is in the range M1b+M2b=30-70% by weight, preferably 30-60% by weight, further preferably 40-50% by weight.

c) Monomer Substituted with at Least One $C_8$-$C_{30}$-Radical

The polymers prepared according to the invention comprise, in polymerized-in form, 0.1 to 20% by weight, preferably 0.1 to 10% by weight, particularly preferably 0.5 to 7.5% by weight of monomer c) substituted with at least one $C_8$-$C_{30}$-radical.

In one or more embodiments, the monomers c) are selected from monomers of the general formulae c1) and c2)

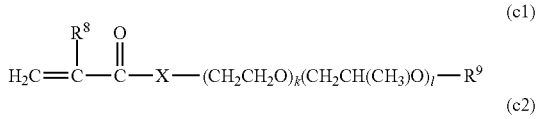

(c1)

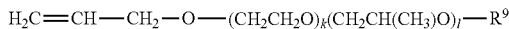

(c2)

where
k and l, independently of one another, are integers in the range from 0 to 1000 and the sum k+l is at least 5,
$R^8$ is hydrogen or $C_1$-$C_4$-alkyl, preferably methyl,
$R^9$ is $C_8$-$C_{30}$-alkyl, $C_8$-$C_{30}$-alkenyl or $C_8$-$C_{30}$-alkylaryl, and
X is O or $NR^{10}$, where $R^{10}$ is selected from H, alkyl, alkenyl, cycloalkyl, heterocycloalkyl, aryl or hetaryl.

In a specific embodiment of the invention, the monomers c) are selected from $C_8$-$C_{30}$-alkyl-substituted monomers.

Directly to X in c1) or to O in c2) is attached either at least one ethylene oxide radical (EO) or at least one propylene oxide radical (PO). In one or more embodiments, at least one EO is attached directly to X and O.

In one embodiment of the invention, the monomers c1) are esters of (meth)acrylic acid, i.e. $R^8$ in formula (c1) is H or preferably $CH_3$, with alkoxylated alcohols.

Suitable alkoxylated alcohols are, for example the alkoxylated
- linear alcohols from natural sources or from the Ziegler build-up reaction of ethylene in the presence of aluminumalkyl catalysts. Examples of suitable linear alcohols are linear $C_8$-$C_{30}$-alcohols, in particular $C_{12}$-$C_{30}$-alcohols. Particularly preferred alcohols which may be mentioned are: n-dodecanol, n-tetradecanol, n-hexadecanol, n-octadecanol, n-eicosanol, n-docosanol, n-tetracosanol, n-hexacosanol, n-octacosanol, and/or n-triacontanol, and also mixtures of the aforementioned alcohols, for example NAFOL® grades such as NAFOL® 22+ (Sasol).
- oxo alcohols such as, for example, isooctanol, isononanol, isodecanol, isoundecanol, isotridecanol (for example Exxal® grades 7, 8, 9, 10, 11, 13).
- alcohols, which are branched in the 2 position; these are the Guerbet alcohols known to the person skilled in the art which are accessible by dimerization of primary alcohols via the so-called Guerbet reaction. Particularly preferred alcohols which may be mentioned here are: Isofol®12 (Sasol), Rilanit®G16 (Cognis).
- alcohols, which are obtained by the Friedel-Crafts-alkylation with oligomerized olefins and which then comprise an aromatic ring as well as a saturated hydrocarbon radical. Particularly preferred alcohols which may be mentioned here are: i-octylphenol and i-nonylphenol.
- alcohols of the general formula (4) of EP 761 780 A2, p. 4

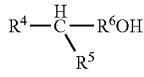

or alcohols of the general formula (5) of EP 761 780 A2, p. 4

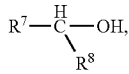

where
$R^4$, $R^5$, $R^7$ and $R^8$ independently of one another, have the meaning described in EP 761 780 A2, p. 4, lines 45 to 58; preferably, $R^4$, $R^5$, $R^7$ and $R^8$ independently of one another, are alkyl radicals having at least 4 carbon atoms and the total number of carbon atoms in the alcohols is at most 30,
$R^6$ is an alkylene radical such as, for example, —$CH_2$—, —$CH_2$—$CH_2$—, —$CH_2$—$CH(CH_3)$—;

For example, 2-decyl-1-tetradecanol may be specified here as a suitable alcohol.

In an embodiment at least one c) is a (meth)acrylic acid ester of a mixture of ethoxylated $C_8$-$C_{30}$-, preferably $C_{12}$-$C_{30}$-, in particular $C_{16}$-$C_{22}$-fatty alcohols.

In an embodiment, at least one c) is a (meth)acrylic acid ester of a mixture of ethoxylated $C_8$-$C_{30}$-, preferably $C_{12}$-$C_{30}$-, in particular $C_{16}$-$C_{22}$-fatty alcohols, where the ethoxylated alcohols in each case comprise 20 to 30 EO-radicals.

In an embodiment, at least one c) is a (meth)acrylic acid ester of a mixture of ethoxylated $C_{12}$-$C_{18}$-fatty alcohols, where the ethoxylated alcohols in each case comprise 10 to 30 EO-radicals. In an embodiment of the invention, c) is or comprises a methacrylic acid ester of a $C_{16}$-$C_{18}$-fatty alcohol ethoxylated with 25 mol of ethylene oxide (also referred to as "$C_{16-18}$-alkyl-PEG1100 methacrylates").

Such $C_{16-18}$-alkyl-PEG1100 methacrylates are commercially available for example as Plex®6877-O (25% strength by weight preparation in methyl methacrylate) or Lutencryl®250 (50% strength by weight solution in methacrylic acid) or VISIOMER® C18 PEG 1105 MA.

In an embodiment of the invention, c) is or comprises a methacrylic acid ester of a $C_{18}$-$C_{22}$-fatty alcohol ethoxylated with 25 mol of ethylene oxide (also referred to as "Beheneth-25 methacrylate", CAS No. 115047-92-2), commercially available for example as Sipomer® BEM.

In a further embodiment of the invention, c) comprises at least two different (meth)acrylic acid esters of ethoxylated $C_8$-$C_{30}$-, preferably ethoxylated $C_{12}$-$C_{30}$-, in particular ethoxylated $C_{16}$-$C_{22}$-fatty alcohols.

The present invention also provides a process according to the invention wherein, c) 0.1 to 20% by weight of an ester of (meth)acrylic acid with at least one alcohol of the general formula (I)

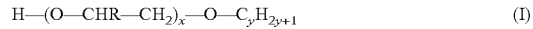

where x is an integer from 10 to 50, y is an integer from 12 to 30 and R is selected from H and $CH_3$, are present in polymerized-in form.

In one or more embodiments, the process according to the invention is one wherein c) comprises at least two different monomers of the formula (I).

In a specific embodiment, the process according to the invention is also one wherein y is an integer from 16 to 22.

Further suitable monomers c) are compounds of the general formula c1), where $R^8$ is H or preferably methyl, X is O, k and l are simultaneously zero and $R^9$ is $C_8$-$C_{20}$-alkylaryl or preferably $C_8$-$C_{20}$-alkyl.

Examples of such monomers a3) are n-octyl(meth)acrylate, 1,1,3,3-tetramethylbutyl (meth)acrylate, 2-ethylhexyl (meth)acrylate, n-nonyl (meth)acrylate, n-decyl (meth)acrylate, isodecyl (meth)acrylate, n-undecyl (meth)acrylate, isoundecyl (meth)acrylate, dodecyl (meth)acrylate, tridecyl (meth)acrylate, myristyl (meth)acrylate, pentadecyl (meth)acrylate, palmityl (meth)acrylate, heptadecyl (meth)acrylate, stearyl (meth)acrylate, lauryl (meth)acrylate, arrachinyl (meth)acrylate, behenyl (meth)acrylate, lignocerenyl (meth)acrylate, cerotinyl (meth)acrylate, melissinyl (meth)acrylate, palmitoleinyl (meth)acrylate, oleyl (meth)acrylate, linolyl (meth)acrylate, linolenyl (meth)acrylate and mixtures thereof.

The weight fraction of the monomer c), which is used in the first polymerization stage, based on the total amount of all monomers to be polymerized during the process according to the invention, is given by M1c.

The weight fraction of the monomer c), which is used in the second polymerization stage, based on the total amount of all monomers to be polymerized during the process according to the invention, is given by M2c.

The total weight fraction of the monomer c), based on the total amount of all monomers to be polymerized during the process according to the invention, is accordingly given by M1c+M2c and is in the range M1c+M2c=0.1-20% by weight, preferably 0.1-15% by weight, particularly preferably 0.5-7.5% by weight.

M1c is preferably at most 0.1*(M1c+M2c), further preferably at most 0.01*(M1c+M2c) and in particular 0. Preferably, the majority or the entire weight fraction of c) is thus polymerized-in during the second polymerization stage.

Monomers d)

The polymers obtainable according to the invention comprise, in polymerized-in form, optionally 0 to 20% by weight of further monomers d), different from a) to c).

Suitable monomers d) are in principle all cosmetically acceptable, radically polymerizable compounds. In particular, suitable monomers d) are also crosslinking compounds with more than one radically polymerizable double bond.

The weight fraction of the monomers d), which is used in the first polymerization stage, based on the total amount of all monomers to be polymerized during the process according to the invention, is given by M1d.

The weight fraction of the monomers d), which is used in the second polymerization stage, based on the total amount of all monomers to be polymerized during the process according to the invention, is given by M2d.

The total weight fraction of the monomers d), based on the total amount of all monomers to be polymerized during the process according to the invention, is accordingly given by M1d+M2d and is in the range M1d+M2d=0-20% by weight, preferably 0-10% by weight, particularly preferably 0.1-7.5% by weight.

The process according to the invention is preferably an emulsion polymerization. The emulsion polymerization per se is a process, known for a long time in the prior art, for preparing polymers in an aqueous phase and requires no further explanation at this point.

The process according to the invention comprises two polymerization stages, the second polymerization stage starting after the first polymerization stage in terms of time.

The first polymerization stage comprises 1.1) the provision of the so-called initial charge comprising the monomer part amounts M1a, M1b, M1c, and M1d, water, optionally further compounds, preferably at least one surface-active agent, 1.2) the heating of the mixture obtained from 1.1) to a temperature in the range from 30 to 120° C., preferably 40 to 90° C., 1.3) the addition of a polymerization initiator.

The second polymerization stage starts after step 1.3) of the first polymerization stage and comprises 2.1) the addition of the monomer part amounts M2a, M2b, M2c, and M2d, to the reaction mixture obtained from 1.3), and 2.2) after-treatment of the reaction mixture obtained from 2.1), such as, for example, reduction of the residual monomers, filtration, at least partial neutralization.

The addition of the monomer part amounts M2a, M2b, M2c and M2d to the reaction mixture obtained from 1.3) which takes place in step 2.1), can take place in different ways according to the invention:

the monomers can be added as separate feeds independently of one another with regard to time and spatial aspects. The individual feeds can be started and ended simultaneously or one after the other;

one part of the monomers can be added together as a mixture, the other part can be added in separate feeds simultaneously or one after the other;

the monomers can all be added together as a mixture in one feed.

A specific embodiment of the invention is the process according to the invention wherein a mixture comprising all part amounts M2i, thus $$\sum_{i=a}^{d} M2i,$$

is added together and simultaneously in one feed. This mixture is particularly preferably an aqueous emulsion comprising all monomer part amounts M2i and at least one surface-active agent.

According to the invention, the following is applicable for the quantitative ratios of the monomers a) and b):

M1b/M1a≥0.4 and M1b/M1a<M2b/M2a.

Furthermore, M1a, M2a, M1b and M2b are in each case greater than zero. Preferably, M2c is also greater than zero.

Preferably M1b/M1a is ≥0.5, further preferably ≥0.6.

According to the invention, at most 40% by weight, preferably at most 25% by weight and particularly preferably at most 12% by weight, of all monomers to be polymerized are present in the reaction space during the first polymerization stage, i.e.

$$\sum_{i=a}^{d} M1i \leq 40\% \text{ by weight,}$$

preferably ≤25% by weight, particularly preferably ≤12% by weight.

An embodiment of the invention is a process for the preparation of polymers comprising, in polymerized-in form a) M1a+M2a=30 to 50% by weight of an ester of (meth)acrylic acid with a $C_1$-$C_4$-alcohol, b) M1b+M2b=30 to 50% by weight of (meth)acrylic acid, c) M1c+M2c=0.1 to 20% by weight of monomers substituted with at least one $C_8$-$C_{30}$-radical, M1d+M2d=0 to 20% by weight of monomers different from a) to c), by emulsion polymerization with a first polymerization stage and a second polymerization stage, wherein M1b/M1a≥0.6 and M1b/M1a<M2b/M2a and $$\sum_{i=a}^{d} M1i \leq 12\% \text{ by weight,}$$

where
M1i are the respective weight fractions of the monomers a) to d) which are present in the reaction space during the first polymerization stage and M2i are the respective weight fractions of the monomers a) to d) which are added during the second polymerization stage and the sum of all weight fractions $$\sum_{i=a}^{d} M1i + \sum_{i=a}^{d} M2i = 100\% \text{ by weight.}$$

The process according to the invention is preferably carried out at pH<7, further preferably at pH<5 and in particular at pH<3.

In one or more embodiments, the polymerization is initiated by a thermally activatable initiator or a redox initiator.

In one or more embodiments, a thermally activatable initiator is used. Suitable thermally activatable radical initiators are primarily those of the peroxy and azo type. These include, inter alia, hydrogen peroxide, peracetic acid, t-butyl hydroperoxide, di-t-butyl peroxide, dibenzoyl peroxide, benzoyl hydroperoxide, 2,4-dichlorobenzoyl peroxide, 2,5-dimethyl-2,5-bis(hydroperoxy)hexane, perbenzoic acid, t-butyl peroxypivalate, t-butyl peracetate, dilauroyl peroxide, dicaproyl peroxide, distearoyl peroxide, dibenzoyl peroxide, diisopropyl peroxydicarbonate, dodecyl peroxydicarbonate, dieicosyl peroxydicarbonate, di-t-butyl perbenzoate, azobisisobutyronitrile, 2,2'-azobis-2,4-dimethylvaleronitrile, ammonium persulfate, potassium persulfate, sodium persulfate and sodium perphosphate.

According to one or more embodiments of the invention, persulfates (peroxodisulfates) are used, in particular sodium persulfate.

When carrying out the emulsion polymerization, the initiator is used in an amount adequate to initiate the polymerization reaction. The initiator is usually used in an amount of about 0.01 to 3% by weight, based on the total weight of the monomers to be polymerized. The amount of initiator is preferably about 0.05 to 2% by weight and in particular 0.1 to 1% by weight, based on the total weight of the monomers to be polymerized.

In an embodiment of the invention, the adequate amount of the initiator is added to the initial charge during the first polymerization stage.

The process according to the invention generally takes place in the presence of an anionic and/or nonionic emulsifier.

Typical emulsifiers are anionic emulsifiers, such as e.g. sodium lauryl sulfate, sodium tridecyl ether sulfate, dioctylsulfosuccinate sodium salt and sodium salts of alkylaryl polyether sulfonates and nonionic emulsifiers such as e.g. alkylaryl polyether alcohols and ethylene oxide-propylene oxide copolymers.

In one or more embodiments, emulsifiers have the general formula R—O—(CH$_2$—CHR'—O)$_n$—X, in which R is C$_6$-C$_{30}$-alkyl, R' is hydrogen or methyl, X is hydrogen or SO$_3$M, M is hydrogen or an alkali metal, and n is a number from 2 to 100.

The polymer dispersion obtained according to the invention can be subjected to a chemical deodorization. For the chemical deodorization, towards the end of the actual emulsion polymerization, further initiator, e.g. a redox initiator, is added. Redox initiators suitable for the chemical deodorization comprise as oxidizing component, for example at least one organic peroxide and/or hydroperoxide such as hydrogen peroxide, tert-butyl peroxide, cumene hydroperoxide, pinane hydroperoxide, diisopropylphenyl hydroperoxide, dibenzoyl peroxide, dilauroyl peroxide and diacetyl peroxide and, as reducing component, for example, alkali metal sulfites, ascorbic acid, acetonebisulfite adduct and/or an alkali metal salt of hydroxymethanesulfinic acid, in which case iron(II) salts, preferably in complexed form, can be added as catalyst.

The polymer dispersions obtainable according to the invention generally have a solids content of from 20 to 60% by weight, in particular about 30 to 40% by weight.

In unneutralized form, the polymer dispersions obtainable according to the invention have a relatively low viscosity. They are therefore easy to handle and can be dosed or pumped around without problems. As a result of neutralization, e.g. to a pH of more than 5, preferably more than 6, in particular 8 to 10, the copolymer becomes soluble and the viscosity of the aqueous medium increases considerably. In this connection, preferably more than 50 mol % of the acid groups are neutralized. Suitable neutralizing agents are e.g. sodium hydroxide, potassium hydroxide, ammonium hydroxide, amines, such as triethylamine, triethanolamine, monoethanolamine, and other alkaline materials.

The non-neutralized dispersions according to the invention have the particular advantage that they can be very readily filtered.

In one or more embodiments, preference is given to non-neutralized dispersions according to the invention wherein 120 liters of the polymer dispersion according to the invention with a solids content of 30% by weight flows, at 25° C. and a preliminary pressure of 1.5 bar through a filter combination of two filters in at most 5 minutes, preferably at most 3 minutes, where the first filter is a nylon monofilament fabric filter with a filter fineness of 125 μm, a diameter of 180 mm, a length of 430 mm and a filter area of ca. 0.25 m$^2$ (product name NMO-125-P015-60M, Eaton), the second filter is a polypropylene needled-felt filter with a filter fineness of 25 μm, a diameter of 180 mm, a length of 430 mm and a filter area of 0.25 m$^2$ (product name PO-25-P01S-60L, Eaton) and the two filters are connected by a hose of length 2 m and a conveyance cross section of 20 mm.

In a specific embodiment, particular preference is given to non-neutralized dispersions according to the invention, wherein 120 liters of the polymer dispersion according to the invention with a solids content of 30% by weight flows, at 25° C. and a preliminary pressure of 1.5 bar, through a filter combination of two filters in at most 5 minutes, preferably at most 3 minutes, where the first filter is a nylon monofilament fabric filter with a filter fineness of ≤125 μm, a diameter of ≤180 mm, a length of ≤430 mm and a filter area of ≤ca. 0.25 m$^2$ (product name NMO-125-P01S-60M, Eaton), the second filter is a polypropylene needled-felt filter with a filter fineness of ≤25 μm, a diameter of ≤180 mm, a length of ≤430 mm and a filter area of ≤ca.0.25 m$^2$ (product name PO-25-P01S-60L, Eaton) and the two filters are joined by a hose of length ≥2 m and a conveyance cross section of ≤20 mm.

The particularly good filterability of the dispersions according to the invention means that large amounts of up to 1200 liters of the non-neutralized dispersions with a solids content of 30% by weight can be filtered under the aforementioned conditions without a filter change being necessary.

Cosmetic Preparations

The invention further relates to cosmetic preparations which comprise the polymers obtainable by the process according to the invention.

Such cosmetic preparations according to the invention are selected, for example, from gel creams, hydroformulations, stick formulations, cosmetic oils and oil gels, mascara, self-tanning agents, face care compositions, body care compositions, after-sun preparations, hair-shaping compositions and hair-setting compositions.

Further cosmetic preparations according to the invention are skin cosmetic preparations in particular, those for caring for the skin. In particular, these are in the form of W/O or O/W skin creams, day and night creams, eye creams, face creams, anti-wrinkle creams, mimic creams, moisturizing creams, bleaching creams, vitamin creams, skin lotions, care lotions, and moisturizing lotions.

Furthermore, the polymers obtainable according to the invention are suitable as ingredients for skin cosmetic preparations such as face toners, face masks, deodorants and other cosmetic lotions and for use in decorative cosmetics, for example as concealing stick, stage make-up, in mascara and eye-shadows, lipsticks, kohl pencils, eyeliners, make-up, foundations, blushers and powders and eyebrow pencils.

Moreover, the polymers obtainable according to the invention can be used in nose strips for pore cleansing, in anti-acne compositions, repellents, shaving compositions, hair removal compositions, intimate care compositions, foot care compositions and also in baby care.

Further prepared preparations according to the invention are washing, showering and bathing preparations which comprise the polymers obtainable according to the invention.

Within the context of this invention, washing, showering and bathing preparations are understood as meaning soaps of liquid to gel-like consistency, such as transparent soaps, luxury soaps, deodorant soaps, cream soaps, baby soaps, skin protection soaps, abrasive soaps and syndets, pasty soaps, soft soaps and washing pastes, liquid washing, showering and bathing preparations, such as washing lotions, shower baths and shower gels, foam baths, oil baths and scrub preparations, shaving foams, lotions and creams.

The cosmetic preparations according to the invention can be in the form of aqueous or aqueous-alcoholic solutions, O/W and W/O emulsions, hydrodispersion formulations, solids-stabilized formulations, stick formulations, PIT formulations, in the form of creams, foams, sprays (pump spray or aerosol), gels, gel sprays, lotions, oils, oil gels or mousse and accordingly be formulated with customary auxiliaries.

The cosmetic preparations according to the invention preferably comprise at least one polymer obtainable according to the invention, at least one cosmetically acceptable carrier and at least one constituent different therefrom which is selected from cosmetically active ingredients, emulsifiers, surfactants, preservatives, perfume oils, further thickeners, hair polymers, hair and skin conditioners, graft polymers, water-soluble or dispersible silicone-containing polymers, photoprotective agents, bleaches, gel formers, care agents, colorants, tinting agents, tanning agents, dyes, pigments, consistency regulators, humectants, refatting agents, collagen, protein hydrolysates, lipids, antioxidants, antifoams, antistats, emollients and softeners.

Hair care compositions preferred according to the invention are selected from pre-treatment compositions, hair rinses, hair conditioners, hair balsams, leave-on hair treatments, rinse-off hair treatments, hair tonics, pomades, styling creams, styling lotions, styling gels, end fluids, hot-oil treatments and foam treatments.

Preferably, the polymers obtainable according to the invention are used as rheology-modifying film formers, hair-setting compositions and conditioners for producing cosmetic, preferably hair cosmetic, preparations.

The invention thus further provides cosmetic, in particular hair cosmetic preparations comprising the polymers obtainable according to the invention.

Preferred hair cosmetic preparations are hair cleansing compositions, shampoos, haircare compositions, hair coloring compositions and hair setting compositions, including in particular hair setting gels.

The polymers obtainable according to the invention are effective particularly as film-forming and/or conditioning rheology modifiers. They are thus specifically suitable for hair setting compositions as "thickening setters" or "setting thickeners" and in haircare compositions as "conditioning thickeners".

In principle, the polymers obtainable according to the invention, in the event of their use in multi-phase preparations such as, for example, O/W and W/O, can be used both in the water phase and also in the oil phase. In general, heterogeneous-phase liquid/liquid preparations comprise the polymers obtainable according to the invention essentially in the water phase.

The invention further provides hair cosmetic compositions comprising
A) at least one polymer obtainable according to the invention,
B) optionally, at least one hair polymer different from A),
C) at least one cosmetically acceptable carrier, and
D) optionally, at least one cosmetically acceptable active ingredient and/or auxiliary different from A) and B).

The polymers obtainable according to the invention in the hair cosmetic compositions also be used as hair-setting component, such that the use of further setting polymers is required only in a reduced amount or may even be entirely superfluous.

The polymers obtainable according to the invention are advantageously also characterized by conditioning properties and are able to improve the sensory properties of hair, e.g. give it suppleness and shine.

The hair cosmetic compositions comprise the polymers obtainable according to the invention preferably in a fraction of from about 0.1 to 10% by weight, particularly preferably 0.2 to 6% by weight, in particular 0.3 to 3% by weight, based on the total weight of the composition.

Examples of suitable hair polymers B) and their preferred amounts are described in detail in WO 2007/010035, p. 68, l.32 to p. 70, l.22. Reference is hereby made to this passage in its entirety.

Preferably, the preparations have a carrier component C), which is selected from water, hydrophilic components, hydrophobic components and mixtures thereof.

Suitable carrier components C) are described in detail in WO 2007/010035, p. 70, l.28 to p. 71, l.37. Reference is hereby made to this passage in its entirety.

Additionally, the compositions according to the invention can comprise, as component D), at least one further cosmetic active ingredient or auxiliary different from A) and B). Suitable components D) are described in detail in WO 2007/010035, p. 72, l.2 to p. 72, l.13. Reference is hereby made to this passage in its entirety.

The polymers obtainable according to the invention can be used together with known thickeners. Suitable thickeners are described in detail in WO 2007/010035, p. 72, l.15 to p. 72, l.24. Reference is hereby made to this passage in its entirety.

Conditioners

The conditioners selected for the cosmetic preparations according to the invention are preferably those conditioners which are described on page 34, line 24 to page 37, line 10 of WO 2006/106140, to which reference is hereby made.

Thickeners

Thickeners suitable for gels, shampoos and haircare compositions are given in "Kosmetik and Hygiene von Kopf bis Fuβ [Cosmetics and Hygiene from Head to Toe]", ed. W. Umbach, 3rd edition, Wiley-VCH, 2004, pp. 235-236, to which reference is made at this point in its entirety. Suitable further thickeners for the cosmetic preparations according to the invention are described for example also on page 37, line 12 to page 38, line 8 of WO 2006/106140, to which reference is hereby made.

Preservatives

Suitable preservatives for the cosmetic preparations according to the invention are described, for example, on page 38, line 10 to page 39, line 18 of WO 2006/106140, to which reference is hereby made.

UV Photoprotective Filters

Suitable UV-photoprotective filters for the cosmetic preparations according to the invention are described, for example on page 39, line 20 to page 41, line 10 of WO 2006/106140, to which reference is hereby made.

Antioxidants

Suitable antioxidants for the cosmetic preparations according to the invention are described, for example, on page 41, line 12 to page 42, line 33 of WO 2006/106140, to which reference is hereby made.

Dispersants

If insoluble active ingredients, e.g. antidandruff active ingredients or silicone oils, are to be dispersed or held permanently in suspension in the preparations according to the invention, preference is given to using dispersants and thickeners such as e.g. magnesium aluminum silicates, bentonites, fatty acyl derivatives, polyvinylpyrrolidone or hydrocolloids, e.g. xanthan gum or carbomers.

The preparations can comprise further additives customary in cosmetics, for example perfume, dyes, refatting agents, complexing and sequestering agents, pearlescent agents, plant extracts, vitamins, active ingredients, pigments which have a coloring effect, softening, moisturizing and/or humectant substances, or other customary constituents such as alcohols, polyols, polymers, organic acids for adjusting the pH, foam stabilizers, electrolytes, organic solvents or silicone derivatives.

With regard to said further ingredients known to the person skilled in the art for the preparations, reference may be made to "Kosmetik and Hygiene von Kopf bis Fuβ" [Cosmetics and Hygiene from Head to Toe]", ed. W. Umbach, 3rd edition, Wiley-VCH, 2004, pp. 123-128, to which reference is hereby made.

The preparations according to the invention such as hair sprays, gels, shampoos and haircare compositions comprise optionally ethoxylated oils selected from the group of ethoxylated glycerol fatty acid esters, particularly preferably PEG-10 olive oil glycerides, PEG-11 avocado oil glycerides, PEG-11 cocoa butter glycerides, PEG-13 sunflower oil glycerides, PEG-15 glyceryl isostearate, PEG-9 coconut fatty acid glycerides, PEG-54 hydrogenated castor oil, PEG-7 hydrogenated castor oil, PEG-60 hydrogenated castor oil, jojoba oil ethoxylate (PEG-26 jojoba fatty acids, PEG-26 jojoba alcohol), glycereth-5 cocoate, PEG-9 coconut fatty acid glycerides, PEG-7 glyceryl cocoate, PEG-45 palm kernel oil glycerides, PEG-35 castor oil, olive oil PEG-7 ester, PEG-6 caprylic acid/capric acid glycerides, PEG-10 olive oil glycerides, PEG-13 sunflower oil glycerides, PEG-7 hydrogenated castor oil, hydrogenated palm kernel oil glyceride PEG-6 ester, PEG-20 corn oil glycerides, PEG-18 glyceryl oleate cocoate, PEG-40 hydrogenated castor oil, PEG-40 castor oil, PEG-60 hydrogenated castor oil, PEG-60 corn oil glycerides, PEG-54 hydrogenated castor oil, PEG-45 palm kernel oil glycerides, PEG-80 glyceryl cocoate, PEG-60 almond oil glycerides, PEG-60 "evening primrose" glycerides, PEG-200 hydrogenated glyceryl palmate, PEG-90 glyceryl isostearate.

Preferred ethoxylated oils are PEG-7 glyceryl cocoate, PEG-9 cocoglycerides, PEG-40 hydrogenated castor oil, PEG-200 hydrogenated glyceryl palmate.

Ethoxylated glycerol fatty acid esters are used for various purposes in aqueous cleansing formulations. Glycerol fatty acid esters with a degree of ethoxylation of ca. 30-50 serve as solubility promoters for nonpolar substances such as perfume oils. Highly ethoxylated glycerol fatty acid esters are used as thickeners.

Active Ingredients

Advantageous active ingredients for the cosmetic preparations according to the invention are described, for example on page 44, line 24 to page 49, line 39 of WO 2006/106140, to which reference is hereby made.

UV Photoprotective Agents

In a preferred embodiment, the preparations according to the invention comprise UV photoprotective agents for protecting the skin and/or the hair. Suitable UV photoprotective agents are described in detail in WO 2006/106114, p. 24, 1.4 to p. 27, 1.27, to which reference is hereby made in its entirety.

Pearlescent Waxes

Suitable pearlescent waxes for the cosmetic preparations according to the invention are described for example on page 50, line 1 to line 16 of WO 2006/106140, to which reference is hereby made.

Emulsifiers

In a preferred embodiment of the invention, the cosmetic preparations according to the invention are present in the form of emulsions. The preparation of such emulsions takes place by known methods. Suitable emulsifiers for the emulsions according to the invention are described for example on page 50, line 18 to page 53, line 4 of WO 2006/106140, to which reference is hereby made.

Perfume Oils

If perfume oils are to be added to the cosmetic preparations according to the invention, then suitable perfume oils are described, for example, on page 53, line 10 to page 54, line 3 of WO 2006/106140, to which reference is hereby made.

Pigments

The cosmetic preparations according to the invention optionally further comprise pigments. Suitable pigments for the preparations according to the invention are described for example on page 54, line 5 to page 55, line 19 of WO 2006/106140, to which reference is hereby made.

Nanoparticles

The preparations according to the invention optionally comprise water-insoluble nanoparticles, i.e. particles with a particle size in the range from 1 to 200, preferably from 5 to 100 nm. Preferred nanoparticles are nanoparticles of metal oxides, in particular of zinc oxide and/or titanium dioxide.

Polymers

In a preferred embodiment, the cosmetic preparations according to the invention also comprise further polymers apart from the polymers obtainable according to the invention. Suitable further polymers are described for example on page 55, line 21 to page 63, line 2 of WO 2006/106140. Reference is hereby made to the content of the cited passage in its entirety.

The polymers obtainable according to the invention are also suitable as rheology-modifying film formers in hair gels, in particular so-called styling gels.

A preferred embodiment of the invention is hair cosmetic preparations, in particular hair setting compositions and hair gels, which, besides the polymers obtainable according to the invention, comprise gel formers customary in cosmetics.

Such further customary gel formers are lightly crosslinked polyacrylic acid, for example carbomer (INCI), cellulose derivatives, e.g. hydroxypropylcellulose, hydroxyethylcellulose, cationically modified celluloses, polysaccharides, e.g. xanthan gum, caprylic/capric triglycerides, sodium acrylates copolymer, polyquaternium-32 (and) paraffinum liquidum (INCI), sodium acrylates copolymer (and) paraffinum liquidum (and) PPG-1 trideceth-6, acrylamidopropyltrimonium chloride/acrylamide copolymer, steareth-10 allyl ether acrylates copolymer, polyquaternium-37 (and) paraffinum liquidum (and) PPG-1 trideceth-6, polyquaternium-37 (and) propylene glycol dicaprate dicaprylate (and) PPG-1 trideceth-6, polyquaternium-7, polyquaternium-44.

Hair Washing Compositions

A specific embodiment of the invention is hair washing compositions and shampoos comprising the polymers obtainable according to the invention.

Depending on hair condition or scalp problem, optionally additional requirements are placed on shampoos and hair washing compositions.

In one or more embodiments, shampoos and hair washing compositions according to the invention comprise anionic surfactants. In a specific embodiment, shampoos and hair washing compositions according to the invention comprise combinations of anionic and ampholytic surfactants. In an embodiment, shampoos and hair washing compositions according to the invention comprise combinations of anionic and zwitterionic surfactants. Further preferred shampoos and cosmetic cleansing compositions according to the invention comprise combinations of anionic and nonionic surfactants.

Suitable surfactants of all types have already been described above under "Surfactants".

In one or more embodiments, anionic surfactants are alkyl sulfates, alkyl polyglycol ether sulfates and ether carboxylic acid salts having 10 to 18 carbon atoms in the alkyl group and up to 12 glycol ether groups in the molecule and sulfosuccinic acid mono- and dialkyl esters having 8 to 18 carbon atoms in the alkyl group and sulfosuccinic acid monoalkyl polyoxyethyl esters having 8 to 18 carbon atoms in the alkyl group and 1 to 6 oxyethyl groups. Particularly preferred anionic surfactants are the alkali metal or ammonium salts of lauryl ether sulfate with a degree of ethoxylation from 2 to 4 EO units.

In a specific embodiment, a zwitterionic surfactant is the fatty acid amide derivative known under the INCI name Cocamidopropyl Betaine.

In one or more embodiments, ampholytic surfactants are N-cocoalkyl aminopropionate, cocoacylaminoethyl aminopropionate and C12-C12-acylsarcosine.

Preferred nonionic surfactants have proven to be the alkylene oxide addition products onto saturated linear fatty alcohols and fatty acids having in each case 2 to 30 mol of ethylene oxide per mole of fatty alcohol or fatty acid. Preparations with excellent properties are likewise obtained if they comprise fatty acid esters of ethoxylated glycerol as nonionic surfactants.

Presentation

The preparations according to the invention can be present, for example, as preparations that can be sprayed form aerosol containers, squeezable bottles or through a pump, spray or foaming device, but also in the form of a composition that can be applied from standard bottles and containers. Suitable propellants for cosmetic or dermatological preparations according to the invention that can be sprayed from aerosol containers are the customarily known readily volatile, liquefied propellants, for example dimethyl ether, hydrocarbons (propane, butane, isobutane), which can be used on their own or in a mixture with one another, for example mixtures of dimethyl ether and isobutane or dimethyl ether and butane. Compressed air, nitrogen, nitrogen dioxide or carbon dioxide or mixtures of these substances can also be used advantageously.

The preparations according to the invention can be prepared in the customary manner by mixing the individual constituents. The pH of the preparations can be adjusted in a known manner by adding acids or bases, preferably by adding buffer mixtures, e.g. based on citric acid/citrate or phosphoric acid/phosphate buffer mixtures. In one embodiment of the invention, the pH is below 10, e.g. in the range from 2-7, in particular in the range from 3-5.

Preferred shampoo formulations comprise
a) 0.05 to 10% by weight of at least one polymer obtainable according to the invention,
b) 25 to 94.95% by weight of water,
c) 5 to 50% by weight of surfactants,
d) 0 to 5% by weight of a conditioning agent,
e) 0 to 10% by weight of further cosmetic constituents.

In a further embodiment, by using the polymers obtainable according to the invention it is also possible to prepare surfactant-reduced formulations with less than 10% by weight of surfactant, based on the preparation, in a viscosity adequate for the preparation.

All anionic, neutral, amphoteric or cationic surfactants customarily used in shampoos and cosmetic cleansing compositions can be used in the shampoos and cosmetic cleansing compositions. Suitable surfactants have been specified above. Particular preference is given to shampoos and cosmetic cleansing compositions with a surfactant content of more than 10% by weight.

In the shampoo formulations, further conditioning agents can be used to achieve certain effects. These include, for example, cationic polymers with the INCI name Polyquaternium, in particular copolymers of vinylpyrrolidone/N-vinylimidazolium salts (Luviquat®FC, Luviquat®HM, Luviquat®MS, Luviquat® are), copolymers of N-vinylpyrrolidone/dimethylaminoethyl methacrylate, quaternized with diethyl sulfate (Luviquat®PQ 11), copolymers of N-vinylcaprolactam/N-vinylpyrrolidone/N-vinylimidazolium salts (Luviquat®Hold); cationic cellulose derivatives (Polyquaternium-4 and -10), acrylamide copolymers (Polyquaternium-7).

Advantageous conditioning agents are, for example, the compounds referred to in accordance with INCI as Polyquaternium (in particular Polyquaternium-1 to Polyquaternium-87).

EXAMPLES

The invention is described in more detail below by examples, without limiting it thereto. Unless stated otherwise, quantitative data in "%" mean percent by weight.

Example 1

The experimental set-up consisted of a 2l reaction vessel with anchor stirrer, reflux condenser and feed vessels.

In the receiver, 360.0 g of demineralized water, 0.6 g of sodium dodecyl sulfate, 6.0 g of methacrylic acid and 9.0 g of ethyl acrylate were heated to 80° C. with stirring (120 rpm).

Upon reaching 80° C., 24.0 g of a 2.5% strength aqueous sodium peroxodisulfate solution were added quickly for the start of the reaction.

5 min after adding the sodium peroxodisulfate solution, a stirred emulsion consisting of
210.0 g of demineralized water
1.65 g of sodium dodecyl sulfate
7.2 g of sorbitan tristearate-20 EO (Tween®80)
30.0 g of methacrylic acid ester of an ethoxylated C16-C18-fatty alcohol mixture (Visiomer® C18 PEG-1105-MA 60% strength)
8.6 g of methacrylic acid ester of an ethoxylated C18-C22-fatty alcohol mixture (Sipomer® BEM 52.5% strength)
136.5 g of methacrylic acid
126.0 g of ethyl acrylate
was metered into the reaction vessel over 1.5 h. After the end of the feed, the experiment was after-stirred for a further 2 h at 80° C. The experiment was then cooled to room temperature. Upon reaching 40° C. during the cooling down process, 0.9 g of a 1% strength aqueous hydrogen peroxide solution was added. 5 min after this addition, 30.0 g of aqueous 0.25% strength L(+)-ascorbic acid were metered in over 30 min.

The pH of the 30.3% strength by weight dispersion (solids content 30.3% by weight) was ca. 2.8.

The dispersion was then filtered off over a 120 μm filter and then filtered off over a filter with mesh width 25 μm. The filterability was very good.

In the filter and sticking to the stirrer, 0.7 g of coagulate could be detected (measured as wet coagulate after squeezing with a dry paper towel).

The dropwise addition (with stirring) of triethanolamine to the milky dispersion diluted beforehand with water (solids content following dilution 5% by weight) produced a water-clear polymer solution from a pH of 7 onwards.

Example 2

The experimental set-up consisted of a 2l reaction vessel with anchor stirrer, reflux condenser and feed vessels.

In the receiver, 720.0 g of completely demineralized water (demin. water), 1.2 g of sodium dodecyl sulfate, 12.0 g of methacrylic acid and 18.0 g of ethyl acrylate were heated to 80° C. with stirring (120 rpm).

Upon reaching 80° C., 48.0 g of a 2.5% strength aqueous sodium peroxodisulfate solution were added rapidly for the start of the reaction.

5 min after the addition of the sodium peroxodisulfate solution, a stirred emulsion consisting of
420.0 g of demineralized water
3.30 g of sodium dodecyl sulfate
14.4 g of sorbitan tristearate-20 EO (Tween®80)
75.0 g of methacrylic acid ester of an ethoxylated C16-C18-fatty alcohol mixture (Visiomer® C18 PEG-1105-MA 60% strength)
273.0 g of methacrylic acid
237.0 g of ethyl acrylate
was metered into the reaction vessel over 1.5 h.

After the end of the feed, the experiment was after-stirred for a further 2 h at 80° C. The experiment was then cooled to room temperature. Upon reaching 40° C. during the cooling down process, 1.8 g of a 1% strength aqueous hydrogen peroxide solution were added. 5 min after this addition, 60.0 g of aqueous 0.25% strength L(+)-ascorbic acid were metered in over 30 min.

The pH of the 30.9% strength by weight dispersion was ca. 2.8. The dispersion was filtered off firstly over a filter with mesh width 120 μm and then over a filter with mesh width 25 μm. The filterability was very good.

In the 120 μm filter and on the stirrer (adhering), 0.9 g of coagulate could be detected (measured as wet coagulate after squeezing with a dry paper towel).

The dropwise addition (with stirring) of triethanolamine to the milky dispersion diluted beforehand with water (solids content following dilution 5% by weight) produced a water-clear polymer solution from a pH of 7 onwards.

Example 3

The experimental set-up consisted of a 2l reaction vessel with anchor stirrer, reflux condenser and feed vessels.

In the receiver, 360.0 g of demineralized water, 0.6 g of sodium dodecyl sulfate, 6.0 g of methacrylic acid and 9.0 g of ethyl acrylate were heated to 80° C. with stirring (120 rpm). Upon reaching 80° C., 24.0 g of a 2.5% strength aqueous sodium peroxodisulfate solution were added rapidly for the start of the reaction.

5 min after the addition of the sodium peroxodisulfate solution, a stirred emulsion consisting of
210.0 g of demineralized water
1.65 g of sodium dodecyl sulfate
7.2 g of sorbitan tristearate-20 EO (Tween®80)
25.0 g of methacrylic acid ester of an ethoxylated C16-C18-fatty alcohol mixture (Visiomer® C18 PEG-1105-MA 60% strength)
139.0 g of methacrylic acid
126.0 g of ethyl acrylate
was metered into the reaction vessel over 1.5 h. After the end of the feed, the experiment was after-stirred for a further 2 h at 80° C. The experiment was then cooled to room temperature. Upon reaching 40° C. during the cooling process, 0.9 g of a 1% strength aqueous hydrogen peroxide solution was added. 5 min after this addition, 30.0 g of aqueous 0.25% strength L(+)-ascorbic acid were metered in over 30 min.

The pH of the 30.3% strength dispersion was ca. 2.8.

The dispersion was then filtered off over a 120 μm filter. The filterability was very good.

In the filter and on the stirrer (adhering), 0.5 g of coagulate could be detected (measured as wet coagulate after squeezing with a dry paper towel).

The dropwise addition (with stirring) of triethanolamine to the milky dispersion diluted beforehand with water (solids content after dilution 5% by weight) produced a water-clear polymer solution from a pH of 7 onwards.

Comparative Example 1

The experimental set-up consisted of a 2l reaction vessel with anchor stirrer, reflux condenser and feed vessels.

In the receiver, 720.0 g of demineralized water, 1.2 g of sodium dodecyl sulfate, 20.0 g of methacrylic acid and 10.0 g of ethyl acrylate were heated to 80° C. with stirring (120 rpm). Upon reaching 80° C., 48.0 g of a 2.5% strength aqueous sodium peroxodisulfate solution were added rapidly for the start of the reaction.

5 min after the addition of the sodium peroxodisulfate solution, a stirred emulsion consisting of
420.0 g of demineralized water
3.30 g of sodium dodecyl sulfate
14.4 g of sorbitan tristearate-20 EO (Tween®80)

75.0 g of methacrylic acid ester of an ethoxylated C16-C18-fatty alcohol mixture (Visiomer® C18 PEG-1105-MA 60% strength)

273.0 g of methacrylic acid 237.0 g of ethyl acrylate was metered into the reaction vessel over 1.5 h. After the end of the feed, the experiment was after-stirred for a further 2 h at 80° C. The experiment was then cooled to room temperature. Upon reaching 40° C. during the cooling process, 1.8 g of a 1% strength aqueous hydrogen peroxide solution were added. 5 min after this addition, 60.0 g of aqueous 0.25% strength L(+)-ascorbic acid were metered in over 30 min.

The pH of the 30.9% strength dispersion was ca. 2.8.

The dispersion was then filtered over a 120 μm filter. Filtration proceeded more slowly than in Examples 1 and 2.

In the 120 μm filter and on the stirrer (adhering), 3 g of coagulate could be detected (measured as wet coagulate after squeezing with a dry paper towel).

The dropwise addition (with stirring) of triethanolamine to the milky dispersion diluted beforehand with water (solids content after dilution 5% by weight) produced a water-clear polymer solution from a pH of ca. 7 onwards.

Comparative Example 2

The experimental set-up consisted of a 2 l reaction vessel with anchor stirrer, reflux condenser and feed vessels.

In the receiver, 720.0 g of demineralized water, 1.2 g of sodium dodecyl sulfate, 5.0 g of methacrylic acid and 25.0 g of ethyl acrylate were heated to 80° C. with stirring (120 rpm).

Upon reaching 80° C., 48.0 g of a 2.5% strength aqueous sodium peroxodisulfate solution were added rapidly for the start of the reaction.

5 min after the addition of the sodium peroxodisulfate solution, a stirred emulsion consisting of 420.0 g of demineralized water 3.30 g of sodium dodecyl sulfate 14.4 g of sorbitan tristearate-20 EO (Tween®80)

75.0 g of methacrylic acid ester of an ethoxylated C16-C18-fatty alcohol mixture (Visiomer® C18 PEG-1105-MA 60% strength)

273.0 g of methacrylic acid 237.0 g of ethyl acrylate was metered into the reaction vessel over 1.5 hours. After the end of the feed, the experiment was after-stirred for a further 2 hours at 80° C. The experiment was then cooled to room temperature. Upon reaching 40° C. during the cooling process, 1.8 g of a 1% strength aqueous hydrogen peroxide solution were added. 5 min after this addition, 60.0 g of aqueous 0.25% strength L(+)-ascorbic acid were metered in over 30 min.

The pH of the 30.9% strength dispersion was ca. 2.8. The dispersion was then filtered off over a 120 μm filter. The filterability was very good.

In the filter and on the stirrer (adhering), 0.8 g of coagulate could be detected (measured as wet coagulate after squeezing with a dry paper towel).

In contrast to the polymers of Examples 1 and 2 according to the invention and of Comparative Example 1, the acidic dispersion could not be dissolved to give a clear solution by adding triethanolamine; it remained cloudy.

Summary of the Results:

|  | E1 | E2 | E3 | C1 | C2 |
|---|---|---|---|---|---|
| M1b/M1a | 0.67 | 0.67 | 0.67 | 2 | 0.2 |
| M2b/M2a | 1.08 | 1.15 | 1.10 | 1.15 | 1.15 |
| M1b/M1a < M2b/M2a | satisfied | satisfied | satisfied | not satisfied | satisfied |
| Coagulate | little | very little | very little | a lot | very little |
| Filterability 120 μm |  |  | very good | poor | very good |
| Filterability 120 μm + 25 μm | very good | very good |  |  |  |
| Clarity | good | good | good | good | poor |
| Methacrylic acid residual monomer | <10 ppm | <10 ppm | <10 ppm | <10 ppm | <10 ppm |

Description of the Tests
Determination of the Viscosity

The viscosity was measured using a viscometer of type Brookfield DV-II+Pro at 20° C. All measurements were carried out a rotational speed of 20 rpm. For the measurements, measuring spindles of the order of magnitude No. 6 or No. 7 were used, depending on the viscosity range.

The viscosity measurement was carried out on the ready-formulated gel in the 250 ml glass pack and was carried out 24 hours after gel manufacture.

Determination of the Clarity

The clarity of a gel was assessed exclusively by means of the human eye. In each case, two people assessed the appearance of the respective standard gel formulation in a 250 ml glass pack under daylight conditions.

Carrying Out the Flexural Test
Preparation of the Samples

The polymer to be tested in each case was incorporated into a gel formulation. 50 g of the gel obtained were made up to 220 g with completely demineralized water (demin. water) and dissolved. The weighed, dry hair tresses (ca. 3 g, 24 cm in length) were immersed into the dilute gel mass. Immersion, removal and wiping-off three times ensured a uniform distribution of the gel solution on the hair.

The excess mass was squeezed off between thumb and index finger, and the hair tress was then adjusted to a weight increase of 1 g-1.4 g (based on the stating weight of the hair tress, depending on the viscosity of the mass) by squeezing between filter paper.

The tresses were then shaped by hand such that they attained an approximately round cross section. At 20° C. and 65% relative humidity, the tresses were dried overnight in a climatically controlled room.

Testing the Flexural Strength

The tests were carried out in each case in a climatically controlled room at 20° C. and 65% relative humidity using a tensile/pressure testing instrument (machine type: TT 2803 E6).

The hair tress was placed symmetrically on two cylindrical rollers (diameter 4 mm, gap=90 mm) in the sample holder. Exactly in the middle, a rounded punch was then used to bend the tress from above ca. 40 mm to the point of breakage of the gel film. The force required for this was measured using a force measuring cell (50 N) and given in Newtons. For a representative flexural test value 7 hair tresses were measured and the average was calculated.

Determination of the Gel Structure

The gel to be tested was applied to a glass plate using a flat spatula and spread uniformly. The applied gel structure was assessed by at least two people. Assessment criteria were, e.g. smooth, grainy, lumpy, rough and clear film formation.

pH Measurement

The pH of the gel was determined using a glass electrode (single-rod measuring chain) at room temperature and in the undiluted gel. Measuring device used: pH meter from Knick, model: Portamess.

Salt Stability (Inclined Plane/Ramp)

Preparation of the Solution

For the investigation of the gels on the inclined plane, the composition of human perspiration was recreated from the following substances:

20.0 g of sodium chloride 17.5 g of ammonium chloride 5.0 g of acetic acid 15.0 g of lactic acid The substances were dissolved in 1.0 liter of demineralized water and adjusted to a pH of 4.8 using sodium hydroxide solution. Before each use, the pH of the solution was tested and, if necessary, corrected to 4.8.

Set-Up and Procedure:

Starting line and target line were marked on a filter paper 6×10 cm in size. The distance between the two lines was 5 cm and corresponded to the run length which the gel covered. As inclined plane, a glass plate was used, which was inserted into a closeable glass container (ca. 60° to 65°). The marked filter paper was placed on this glass plate and saturated with 4 ml of the synthetic perspiration solution and/or demin. water. It was ensured that the filter paper was wetted evenly. Approximately 0.3 g of the gel to be investigated in each case was applied to the paper saturated with solution. A stopwatch was used to measure the time which the gel required to flow 5 cm on the plane. In the FIGURE, the experimental set-up is shown diagrammatically.

In order to determine the base value of an individual gel, the experiment was carried out firstly with demin. water as flow agent. If the gel had still not reached the target position after 15 minutes, the experiment was terminated. The time and the distance covered were documented.

The experiment was then repeated using synthetic perspiration as flow agent. The time which the gel required to cover the 5 cm was noted. Each experiment (with demin. water and synthetic perspiration) was carried out four times, and the average value and the relative standard deviation were calculated.

Hair Gels

The hair gels according to the invention presented below were prepared as follows:

Firstly, the components of phase A were solubilized. Phase B was then prepared and dissolved, then added to phase A, and a combined solution was prepared with stirring.

Phase C was then added to phase A+B and the mixture was stirred to homogeneity.

The stated amounts are in % by weight unless expressly described otherwise.

Dispersion 1 is the filtered polymer dispersion of example 1 according to the invention.

Instead of dispersion 1 in all of the following formulations, any desired polymer dispersion according to the invention can be used, in particular also the polymer dispersions of examples 2 and 3 according to the invention.

Hair Gel 1

| Ingredient | INCI (manufacturer) |
|---|---|
| | Phase A |
| 0.40 Cremophor ® CO40 | PEG-40 Hydrogenated castor oil |
| 0.10 perfume oil | |
| 81.09 water dist. | Aqua dem. |
| | Phase B |
| 15.00 Luviskol ® K90 (3% polymer content) | PVP |
| 2.57 Dispersion 1 (0.8% WS) | |
| 0.50 Euxyl ® PE 9010 | Phenoxyethanol Ethylhexyl Glycerin |
| | Phase C |
| 0.34 AMP | 2-Amino-2-Methyl-propanol |

Test data:
Viscosity 37 100 mPas (Brookfield ® RVD VII+)

Hair Gel 2

| Ingredient | INCI (manufacturer) |
|---|---|
| | Phase A |
| 0.40 Cremophor ® CO40 | PEG-40 Hydrogenated Castor Oil |
| 0.10 perfume oil | |
| 85.45 water dist. | Aqua dem. |
| | Phase B |
| 10.00 Luviskol ® VA64W (5% polymer content) | PVP/VA |
| 3.21 Dispersion 1 (1.0% polymer content) | |
| 0.50 Euxyl ® PE 9010 | Phenoxyethanol Ethylhexyl Glycerin |
| | Phase C |
| 0.34 AMP | 2-Amino-2-Methyl-propanol |

Test data:
Viscosity 38 900 mPas (Brookfield RVD VII+)
pH 7.10

Hair Gel 3

| Ingredient | INCI (manufacturer) |
|---|---|
| | Phase A |
| 0.40 Cremophor ® CO40 | PEG-40 Hydrogenated Castor Oil |
| 0.10 perfume oil | |
| 80.45 water dist. | Aqua dem. |
| | Phase B |
| 15.00 Luviset ® Clear (3% polymer content) | VP/Methacrylamide/N-Vinyl Imidazole Polymer |
| 3.21 Dispersion 1 (1.0% polymer content) | |
| 0.50 Euxyl ® PE 9010 | Phenoxyethanol Ethylhexyl Glycerin |
| | Phase C |
| 0.34 AMP | 2-Amino-2-Methyl-propanol |

Test data:
Viscosity 40 000 mPas (Brookfield RVD VII+)
pH 7.10

Hair Gel 4

| Ingredient | INCI (manufacturer) |
|---|---|
| Phase A | |
| 0.40 Cremophor ® CO40 | PEG-40 Hydrogenated Castor Oil |
| 0.10 perfume oil | |
| 85.45 water dist. | Aqua dem. |
| Phase B | |
| 2.50 Luviquat ® Supreme (0.5% polymer content) | Polyquaternium-68 |
| 7.50 Luviset ® Clear (1.50% polymer content) | VP/Methacrylamide/N-Vinyl Imidazole Polymer |
| 3.21 Dispersion 1 (1.0% polymer content) | |
| 0.50 Euxyl ® PE 9010 | Phenoxyethanol Ethylhexyl Glycerin |
| Phase C | |
| 0.34 AMP | 2-Amino-2-Methyl-propanol |

Test data:
Viscosity 56 600 mPas (Brookfield RVD VII+)
pH 7.20
Flexural test 200 cN

Hair Gel 5

| Ingredient | INCI (manufacturer) |
|---|---|
| Phase A | |
| 0.40 Cremophor ® CO40 | PEG-40 Hydrogenated Castor Oil |
| 0.10 perfume oil | |
| 77.95 water dist. | Aqua dem. |
| Phase B | |
| 2.50 Luviquat ® Supreme (0.5% polymer content) | Polyquaternium-68 |
| 15.00 Luviskol ® K90 (3.0% polymer content) | PVP |
| 3.21 Dispersion 1 (1.0% polymer content) | |
| 0.50 Euxyl ® PE 9010 | Phenoxyethanol Ethylhexyl Glycerin |
| Phase C | |
| 0.34 AMP | 2-Amino-2-Methyl-propanol |

Test data:
Viscosity 68 800 mPas (Brookfield RVD VII+)
pH 7.12
Flexural test 196 cN

Hair Gel 6

| Ingredient | INCI (manufacturer) |
|---|---|
| Phase A | |
| 0.40 Cremophor ® CO40 | PEG-40 Hydrogenated Castor Oil |
| 0.10 perfume oil | |
| 82.95 water dist. | Aqua dem. |
| Phase B | |
| 2.50 Luviquat ® Supreme (0.5% polymer content) | Polyquaternium-68 |
| 1.00 Luviskol ® VA64 (5.0% polymer content) | PVP/VA |
| 3.21 Dispersion 1 (1.0% polymer content) | |
| 0.50 Euxyl ® PE 9010 | Phenoxyethanol Ethylhexyl Glycerin |
| Phase C | |
| 0.34 AMP | Amino-2-Methyl-propanol |

Test data:
Viscosity 41 750 mPas (Brookfield RVD VII+)
pH 6.90
Flexural test 166 cN

Hair Gel 7

| Ingredient | INCI (manufacturer) |
|---|---|
| Phase A | |
| 0.30 Cremophor ® CO40 | PEG-40 Hydrogenated Castor Oil |
| 0.10 perfume oil | |
| 79.84 water dist. | Aqua dem. |
| Phase B | |
| 10.00 Luviset ® Clear (2.0% polymer content) | VP/Methacrylamide/N-Vinyl Imidazole Polymer |
| 3.33 Dispersion 1 (1.0% polymer content) | |
| 2.50 Karion ®F | Sorbitol |
| 2.50 1,2-propylene glycol Care | Propylene glycol |
| 0.50 Panthenol 50P | Panthenol |
| 0.10 Niacinamide | Niacinamide (Nutrilo) |
| 0.50 Euxyl ®PE 9010 | Phenoxyethanol Ethylhexyl Glycerin |
| Phase C | |
| 0.33 AMP | 2-Amino-2-Methyl-propanol |

Test data:
Viscosity 45 200 mPas (Brookfield RVD VII+)
pH 7.30
Flexural test 236 cN
Curl retention 89%

Hair Gel 8

| Ingredient | INCI (manufacturer) |
|---|---|
| Phase A | |
| 0.30 Cremophor ® CO40 | PEG-40 Hydrogenated Castor Oil |
| 0.10 perfume oil | |
| 74.84 water dist. | Aqua dem. |
| Phase B | |
| 5.00 Luviskol ®VA 64W (2.5% polymer content) | PVP/VA Copolymer |
| 10.00 Luviset ®Clear (2.0% polymer content) | VP/Methacrylamide/N-Vinyl Imidazole Polymer |
| 3.33 Dispersion 1 (1.0% polymer content) | |
| 2.50 Karion ®F | Sorbitol |
| 2.50 1,2-propylene glycol care | Propylene glycol |
| 0.50 Panthenol 50P | Panthenol |
| 0.10 Niacinamide | Niacinamide (Nutrilo) |
| 0.50 Euxyl ®PE 9010 | Phenoxyethanol Ethylhexyl Glycerin |
| Phase C | |
| 0.33 AMP | 2-Amino-2-Methyl-propanol |

Test data:
Viscosity 37 800 mPas (Brookfield RVD VII+)
pH 7.20

Comparison of different thickeners in preparations with PVP (Luviskol® K90)

| INCI | Thickener fraction (%) | Viscosity (mPas) | pH | Clarity | Flexural test (cN) | Structure smooth/ rough Grade 1-4 | Salt compatibility |
|---|---|---|---|---|---|---|---|
| Polymer as in Example 1 | | 1% | 64 400 | 6.97 | clear | 175 ± 14 | smooth | Yes |
| Aculyn ®22 | Acrylates/ Steareth-20 Methacrylate Copolymer | 1% | 30 700 | 7.08 | clear | 150 ± 15 | smooth | Yes |
| Aculyn ®28 | Acrylates/ Beheneth-25 Methacrylate Copolymer | 1% | 120 000 | 7.19 | almost clear | 198 ± 15 | rough | Yes |
| Aculyn ®33 | Acrylates Copolymer | 1% | 5920 | 7.00 | cloudy | 75 ± 6 | smooth | No |
| Aculyn ®88 | Acrylates Copolymer | 1% | 12 380 | 7.08 | clear | 74 ± 6 | smooth | No |
| Structure ® 3001 | Acrylates/ Ceteth-20- Itacone Copolymer | 1% | 3560 | 7.13 | clear | 119 ± 7 | smooth | Yes |
| Salcare ® SC80 | Steareth-10 Allylether Acrylates Copolymer | 1% | 13 840 | 6.93 | clear | 129 ± 14 | smooth | Yes |
| Salcare ® SC81 | Acrylates Copolymer | 1% | 9300 | 7.14 | cloudy | 81 ± 14 | smooth | No |
| Tinovis ® GTC | Acrylates/ Beheneth-25 Methacrylate Copolymer | 1% | 110 000 | 7.00 | clear | 171 ± 13 | rough | Yes |
| Carbopol ® 980 | Carbomer | 0.5% | 78 800 | 7.03 | cloudy | 97 ± 8 | almost smooth | No |

Result: Only the polymer obtainable according to the invention permits in hair gels the combination of the important application properties, solution viscosity, clarity of the gel, high setting power, smooth gel structure and salt compatibility.

Hair Shampoos

The stated amounts are in % by weight unless expressly described otherwise. Dispersion 1 is the filtered polymer dispersion of example 1 according to the invention.

Conditioning Shampoo with Jaguar® C 13S and Silicones

| Ingredient | INCI(manufacturer) |
|---|---|
| Phase A | |
| 0.20 Jaguar ®C 13 S | Guar Hydroxypropyltrimonium Chloride |
| 62.00 water dist. | Aqua dem. |
| Phase B | |
| 17.50 Texapon ®N 701 (12%) | Sodium laureth Sulfate |
| 5.40 Tego ®Betain L7 (1.6%) | Cocoamidopropyl Betaine (Evonik) |
| Phase C | |
| 1.60 Dispersion 1 | |
| q.s. NaOH 20% | Sodium Hydroxide |
| Phase D | |
| 2.20 Dow Corning ®Dispersion 1785 (1.3%) | Dimethiconol, TEA-Dodecylbenzenesulfonate |
| 1.10 Dow Corning ®Emulsion CE-8170 (0.2%) | Amodimethocone, C11-15 Pareth-7, Glycerin, Trideceth-12 |
| 9.10 Euperlan ®3000 AM (2%) | Glycol Distearate, Laureth-4, Cocoamidopropyl Betaine |
| 0.20 perfume oil | |
| 0.20 Glydant ® LTD. | DMDM Hydantoin |

-continued

| Ingredient | INCI(manufacturer) |
|---|---|
| Phase E | |
| q.s. Citric acid | Citric Acid |
| 0.50 Sodium chloride | Sodium Chloride |

Preparation:
The components of phase A were dissolved. Phase B was prepared and added to phase A. Phase C was added to phase A + B and the pH was adjusted to approximately 6.7 with stirring. Phase D was stirred homogeneously into the mixture A + B + C.
The pH of the resulting mixture was adjusted to approximately pH 6.0 with citric acid, sodium chloride was added and everything was stirred until homogeneous.
Test data:
Viscosity 5300 mPas (Brookfield RVD VII+)
pH 6.10

Conditioning Shampoo with UCARE® Polymer 400C and Silicones

| Ingredient | INCI(manufacturer) |
|---|---|
| Phase A | |
| 0.20 UCARE ® Polymer JR 400 | Polyquaternium-10 |
| 62.00 water dist. | Aqua dem. |
| Phase B | |
| 17.50 Texapon ®N 701 (12%) | Sodium Laureth Sulfate |
| 5.40 Tego ®Betain L7 (1.6%) | Cocoamidopropyl Betaine (Evonik) |
| Phase C | |
| 1.60 Dispersion 1 | |
| q.s. NaOH 20% | Sodium Hydroxide |
| Phase D | |
| 2.20 Dow Corning ®Dispersion 1785 (1.3%) | Dimethiconol, TEA-Dodecylbenzenesulfonate |

| Ingredient | INCI(manufacturer) |
|---|---|
| 1.10 Dow Corning ®Emulsion CE-8170 (0.2%) | Amodimethocone, C11-15 Pareth-7, Glycerin, Trideceth-12 |
| 9.10 Euperlan ®3000 AM (2%) | Glycol Distearate, Laureth-4, Cocamidopropyl Betaine |
| 0.20 perfume oil | |
| 0.20 Glydant ® LTD. | DMDM Hydantoin |
| Phase E | |
| q.s. Citric acid | Citric Acid |
| 0.50 Sodium chloride | Sodium Chloride |

Preparation:
The components of phase A were dissolved. Phase B was prepared and added to phase A. Phase C was added to phase A + B and the pH was adjusted to approximately 6.7 with stirring. Phase D was stirred homogeneously into the mixture A + B + C.
The pH of the resulting mixture was adjusted to approximately pH 6.0 with citric acid, sodium chloride was added and everything was stirred until homogeneous.
Test data:
Viscosity 4800 mPas (Brookfield RVD VII+)
pH 5.95

Conditioning Shampoo with Lower Surfactant Fraction

| Ingredient | INCI(manufacturer) |
|---|---|
| Phase A | |
| 3.30 Dispersion 1 | |
| 59.80 water dist. | Aqua dem. |
| q.s. NaOH 20% | Sodium Hydroxide |
| Phase B | |
| 0.10 Salcare ®CS 60 | Acrylamidopropyltrimonium Chloride |
| 2.90 water dist. | Aqua dem. |
| Phase C | |
| 25.80 Texapon ®NSO (7% surfactant fraction) | Sodium Laureth Sulfate |
| 6.80 Tego ®Betain L7 (2.0% surfactant fraction) | Cocoamidopropyl Betaine |
| 0.30 perfume | |
| q.s. preservative | |
| Phase D | |
| q.s. Citric acid | Citric Acid |
| 0.50 Sodium chloride | Sodium chloride |

Preparation:
The components of phase A were weighed in and dissolved, then adjusted to approximately pH 6.7 with NaOH. Phase B was weighed in and dissolved then added to phase A. The components of phase C were added to phase A + B and homogeneously stirred. The pH was then adjusted to approximately pH 6.0 with citric acid, sodium chloride was added and the mixture was stirred until homogeneous.
Test data:
Viscosity 5340 mPas (Brookfield RVD VII+)
pH 5.9

Anti-Dandruff Shampoo with Zinc Pyrithione

| Ingredient | INCI(manufacturer) |
|---|---|
| Phase A | |
| 3.20 Dispersion 1 | |
| 41.00 water dist. | Aqua dem. |
| q.s. NaOH 20% | Sodium Hydroxide |
| Phase B | |
| 0.80 Luviquat ®Sensation (0.2% polymer fraction) | Polyquaternium-87 |
| 2.90 water dist. | Aqua dem. |
| Phase C | |
| 35.70 Texapon ®NSO (9.7% surfactant fraction) | Sodium Laureth Sulfate |
| 12.50 Tego ®Betain L7 (3.7% surfactant fraction) | Cocoamidopropyl Betaine |

| Ingredient | INCI(manufacturer) |
|---|---|
| 2.50 Zink-Pyrion ® 48% Micro (1.2% active fraction) | Zinc Pyrithione |
| Phase D | |
| 0.30 perfume | |
| q.s. preservative | |
| Phase E | |
| q.s Citric acid | Citric Acid |

Preparation:
The components of phase A were weighed in and dissolved, then adjusted to approximately pH 6.7 with NaOH. Phase B was weighed in and dissolved, then added to phase A. The components of phase C were added to phase A + B and stirred until homogeneous. Phase D was then added and the resulting mixture was homogenized. Finally, the pH was adjusted to approximately pH 6.0 with citric acid.
Test data:
Viscosity 12 280 mPas (Brookfield RVD VII+)
pH 6.2

Conditioning Shampoo with Luviquat® Sensation, Uvinul® MC 80

| Ingredient | INCI(manufacturer) |
|---|---|
| Phase A | |
| 2.00 Luviquat ®Sensation (0.5% polymer fraction) | Polyquaternium-87 |
| 48.30 water dist. | Aqua dem. |
| q.s. preservative | Preservative |
| Phase B | |
| 8.90 Dehyton ®PK 45 | Cocamidopropyl Betaine |
| 35.70 Texapon ®NSO (9.7% surfactant fraction) | Sodium Laureth Sulfate |
| Phase C | |
| 1.60 Dispersion 1 (0.5% thickener fraction) | |
| q.s. NaOH 20% | Sodium Hydroxide |
| Phase D | |
| 0.50 D-Panthenol ®USP | Panthenol |
| 2.00 Uvinul ®MC 80 | Ethylhexyl Methoxycinnamate |
| 0.30 perfume oil | Perfume |
| 0.10 Edeta BD | Disodium EDTA |
| Phase E | |
| 0.70 Sodium chloride | Sodium Chloride |

Preparation:
The components of phase A were weighed in and mixed. Phase B was added in succession to phase A and dissolved. The components of phase C were added to phase A + B, the pH was adjusted to ca. pH 6 and stirred to homogeneity. Phase D was added and dissolved. The viscosity was adjusted with phase E.
Test data:
Viscosity 4010 mPas (Brookfield RVD VII+)
pH 5.91
Reduction in wet combability 70% ± 5%

Conditioning Shampoo with Salcare® SC 60

| Ingredient | INCI (manufacturer) |
|---|---|
| Phase A | |
| 0.10 Salcare ®SC 60 | Acrylamidepropyltrimonium Chloride, Acrylamide |
| 15.00 water dist. | Aqua dem. |
| q.s. preservative | Preservative |
| Phase B | |
| 1.60 Dispersion 1 (0.5% thickener fraction) | |
| 33.30 water dist. | Aqua dem. |
| q.s. NaOH 20% | Sodium Hydroxide |

-continued

| Ingredient | INCI (manufacturer) |
|---|---|
| Phase C | |
| 8.90 Dehyton ®PK 45 | Cocamidopropyl Betaine |
| 35.70 Texapon ®NSO | Sodium Laureth Sulfate |
| (9.7% surfactant fraction) | |
| Phase D | |
| 0.50 D-Panthenol ®USP | Panthenol |
| 4.00 Dow Corning ®1664 | Dimethicone. Laureth-4, Laureth-23 |
| 0.30 perfume oil | Perfume |
| Phase E | |
| 0.50 Sodium chloride | Sodium Chloride |

Preparation:
The components of phase A were weighed in and dissolved. Phase B was weighed in and neutralized with NaOH. Phase C was added to phase B, and stirred until homogeneous. The dissolved phase A was then added to phase B + C and stirred until homogeneous. The pH was adjusted to ca. pH = 6. Phase D was added and dissolved. Phase E was used to adjust the viscosity.
Test data:
Viscosity 4920 mPas (Brookfield RVD VII+)
pH 6.04
Reduction in wet combability 74% ± 4%

Hair Color Formulation—Developer

| Ingredient' | INCI(manufacturer) |
|---|---|
| Phase A | |
| 80.00 water dist. | Aqua dem. |
| 0.15 Disodium Phosphate | Disodium Phosphate |
| Phase B | |
| 5.00 Dispersion 1 | |
| (1.6% thickener fraction) | |
| Phase C | |
| 12.00 Hydrogen peroxide (50%) | Hydrogen Peroxide |
| 1.00 Glycerol (99%) | Glycerin |
| 1.00 Texapon ®NSO | Sodium Laureth Sulfate |
| (0.27% surfactant fraction) | |
| Phase D | |
| q.s. Sequestrante HEDP | Etidronic Acid |

Preparation:
The components of phase A were weighed in and dissolved. The components of phases B and C were then added to phase A and stirred. Phase D was used to adjust the pH to 2.5 to 3.
Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as disclosed.

What is claimed is:

1. A process for the preparation of polymers, the polymers comprising in a polymerized-in form,
    a. M1a+M2a=30 to 70% by weight of an ester of (meth)acrylic acid with a C1-C4-alcohol;
    b. M1b+M2b=30 to 70% by weight of (meth)acrylic acid;
    c. M1c+M2c=0.1 to 20% by weight of monomer substituted with at least one C8-C30-radical; and
    M1d+M2d=0 to 20% by weight of monomers different from a) to c),
    the process comprising emulsion polymerization with a first polymerization stage followed by a second polymerization stage,
    wherein the first polymerization stage includes
    i) providing an initial charge comprising the monomer part amounts M1a, M1b, M1c, and M1d, water, and optionally a surface-active agent, to form a first monomer mixture;
    ii) heating the first monomer mixture (i) to a temperature in the range of about 30 to 120° C.; and
    iii) adding a polymerization initiator to form a first reaction mixture, and
    wherein the second polymerization stage includes
    iv) adding the monomer part amounts M2a, M2b, M2c, and M2d to the first reaction mixture (iii) to form a second reaction mixture; and
    v) after-treatment of the second reaction mixture (iv),
    wherein
    M1b/M1a≥0.4 and
    M1b/M1a<M2b/M2a and $$\sum_{i=a}^{d} M1i \leq 40\% \text{ by weight,}$$

wherein
    M1i are the representative weight fractions of the monomers a) and d), which are present in the reaction space during the first polymerization stage and M2i are the representative weight fractions of the monomer a) to d), which are added during the second polymerization stage and the sum of all weight fractions $$\sum_{i=a}^{d} M1i + \sum_{i=a}^{d} M2i = 100\% \text{ by weight.}$$

2. The process according to claim 1, wherein a) comprises ethyl acrylate.

3. The process according to claim 1, wherein b) comprises methacrylic acid.

4. The process according to claim 1, wherein
    c) 0.1 to 20% by weight of an ester of (meth)acrylic acid with at least one alcohol of the general formula (I)

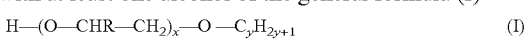  (I)

wherein x is an integer from 10 to 50, y is an integer from 12 to 30 and R is selected from H and $CH_3$, are present in polymerized-in form.

5. The process according to claim 4, wherein c) comprises at least two different monomers of the formula (I).

6. The process according to claim 4, wherein y is an integer from 16 to 22.

7. The process according to claim 1, wherein the emulsion polymerization is carried out at pH <7.

8. The process according to claim 1, wherein the emulsion polymerization is caned out at pH <5.

9. The process according to claim 1, wherein $$\sum_{i=a}^{d} M1i \leq 25\% \text{ by weight.}$$

10. A method of preparing an aqueous preparation, the method comprising using the polymer obtainable by the process of claim 1 as a thickener.

11. The process according to claim 2, wherein b) comprises methacrylic acid.

12. The process according to claim 2, wherein
    c) 0.1 to 20% by weight of an ester of meth(acrylic acid) with at least one alcohol of the general formula (I)

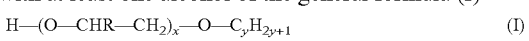  (I)

wherein x is an integer from 10 to 50, y is an integer from 12 to 30 and R is selected from H and CH$_3$, are present in polymerized-in form.

13. The process according to claim 5, wherein y is an integer from 16 to 22.

14. The process according to claim 2, wherein the emulsion polymerization is carried out at a pH <7.

15. The process according to claim 2, wherein the emulsion polymerization is carried out at a pH <5.

16. The process according to claim 2, wherein $$\sum_{i=a}^{d} M1i \leq 25\% \text{ by weight.}$$

17. The process according to claim 3, wherein
c) 0.1 to 20% by weight of an ester of (meth)acrylic acid with at least one alcohol of the general formula (I)

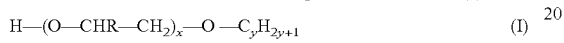    (I)

wherein x is an integer from 10 to 50, y is an integer from 12 to 30 and R is selected from H and CH$_3$, are present in polymerized-in form.

18. The process according to claim 17, wherein c) comprises at least two different monomers of formula (I).

19. The process according to claim 18, wherein y is an integer from 16 to 22.

* * * * *